(12) United States Patent
Lambert et al.

(10) Patent No.: US 10,191,027 B2
(45) Date of Patent: Jan. 29, 2019

(54) METHODS OF DETERMINING PROPERTIES OF OIL

(71) Applicants: TOPNIR SYSTEMS SAS, Aix en Provence (FR); OPTA-PERIPH, Enghien (FR)

(72) Inventors: Didier Lambert, Bernos Baeulac (FR); Claude Saint Martin, Pelissane (FR); Miguel Sanchez, Lavera (FR); Bernard Ribero, Peyrolles en Provence (FR); Pierre Barere, Enghien les Bains (FR)

(73) Assignees: TOPNIR SYSTEMS SAS, Aix en Provence (FR); OPTA-PERIPH, Enghien (FR)

( * ) Notice: Subject to any disclaimer, the term of this patent is extended or adjusted under 35 U.S.C. 154(b) by 68 days.

(21) Appl. No.: 15/502,869

(22) PCT Filed: Aug. 3, 2015

(86) PCT No.: PCT/EP2015/067824
§ 371 (c)(1),
(2) Date: Feb. 9, 2017

(87) PCT Pub. No.: WO2016/023779
PCT Pub. Date: Feb. 18, 2016

(65) Prior Publication Data
US 2017/0227516 A1 Aug. 10, 2017

(30) Foreign Application Priority Data
Aug. 11, 2014 (EP) .................................. 14290241

(51) Int. Cl.
*G01N 21/84* (2006.01)
*G01N 33/28* (2006.01)
(Continued)

(52) U.S. Cl.
CPC ....... *G01N 33/2823* (2013.01); *G01N 21/359* (2013.01); *G01N 21/3577* (2013.01); *G01N 21/85* (2013.01); *G01N 2001/2064* (2013.01)

(58) Field of Classification Search
CPC ............. G01N 33/2823; G01N 21/359; G01N 2001/2064
See application file for complete search history.

(56) References Cited

U.S. PATENT DOCUMENTS

2008/0211505 A1 * 9/2008 Trygstad ................ G01N 24/08 324/321

FOREIGN PATENT DOCUMENTS

| GB | 2030963 A | | 4/1980 |
| WO | WO 2011/097373 | * | 8/2011 |
| WO | 2013126732 A1 | | 8/2013 |

OTHER PUBLICATIONS

"A Swagelok Pre-Engineered Subsystem", Fast Loop Module Application Guide, Dec. 31, 2012, Retrieved from http://www.swagelok.com/downloads/WebCatalogs/EN/MS-02-361.pdf on Oct. 29, 2014.
(Continued)

*Primary Examiner* — Yara B Green
(74) *Attorney, Agent, or Firm* — Maschoff Brennan

(57) ABSTRACT

This invention concerns methods of determining properties of oil, especially crude oil with a spectrometer. This invention also concerns a crude oil analytical and single or multi-stream sampling device which is particularly suitable for the online measurement of crude oil properties with a spectrometer (8). This invention further concerns a crude oil sampling procedure which is particularly suitable for the online measurement of crude oil properties with a spectrometer.

20 Claims, 7 Drawing Sheets

(51) Int. Cl.
    *G01N 21/85*     (2006.01)
    *G01N 21/3577*   (2014.01)
    *G01N 21/359*    (2014.01)
    *G01N 1/20*     (2006.01)

(56) References Cited

OTHER PUBLICATIONS

"Welker Catalog", Dec. 31, 2010, Retrieved from http://welker.com/sites/default/files/WelkerCatalog.pdf on Oct. 29, 2014, pp. 24-27.

\* cited by examiner

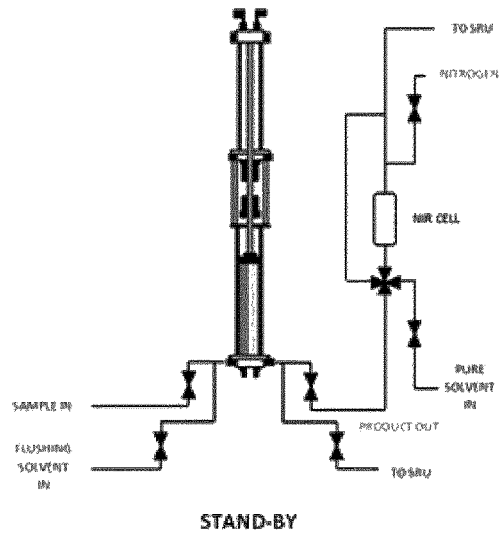
Figures 5a
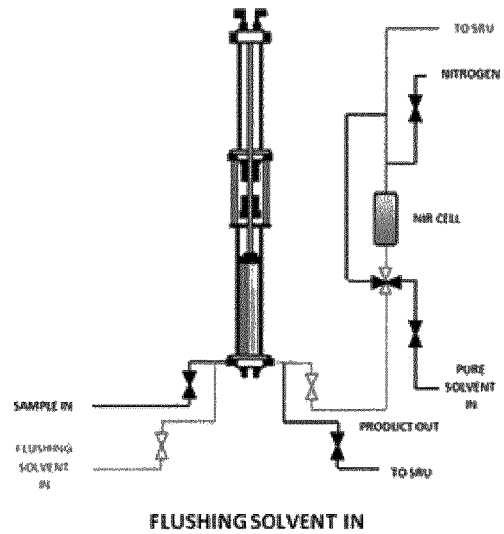
Figure 5b
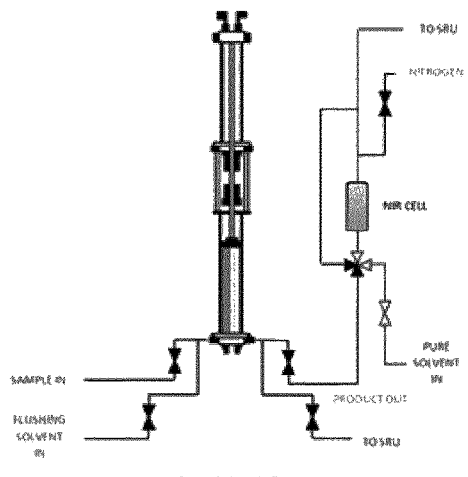
Figures 5c
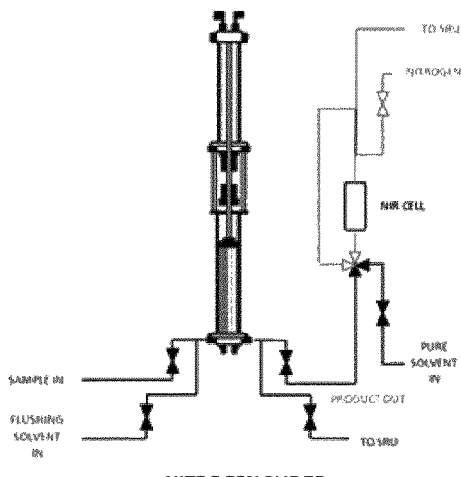
Figure 5d
Figure 5

METHODS OF DETERMINING PROPERTIES OF OIL

BACKGROUND

This invention concerns methods of determining properties of oil, especially crude oil with a spectrometer. This invention also concerns a crude oil analytical and sampling device which is particularly suitable for the online measurement of crude oil properties with a spectrometer. This invention further concerns a crude oil sampling procedure which is particularly suitable for the online measurement of crude oil properties with a spectrometer.

Many properties of crude oil (chemical, physical and/or physic-chemical) are regularly determined on a very large scale worldwide, especially gas content and percentage of naphtha, gas oil and fuel oil, the latter being a key parameter in assessing the value of any oil. These determinations are usually done off line by mechanical techniques e. g. by distillation and/or chromatography.

WO9836274 discloses a method of controlling a separation of a component in crude oil, e.g. downstream of a well head, in which the oil is analysed, e.g. by near infra-red (NIR) spectroscopy, at or before a pipeline between the analyser and separator especially a line at least 10 km long and the results used to optimise the separation. The corresponding NIR spectroscopy is also used to determine a property, e.g. composition of a crude oil, in particular its content of naphtha, gas oil and/or fuel oil.

A catalog from the Welker Engineering Company includes pages 24-27 that relate to crude oil sampling products comprising e.g. a sampler and a crude oil container.

URL:http://www.swagelok.com/downloals/WebCatalogs/EN/MS-02-361.pdf, as retrieved on 2014 Oct. 29, is a catalog from the Swagelok Instrumentation Company which relates to fast loop modules which are designed to handle high flows in sample transport lines to reduce time delays for online analyser systems.

GB2030963 claims a method of obtaining a homogeneous sample from a liquid transfer line (for example a crude oil pipeline) comprising removing liquid from the transfer line and returning it to the transfer line through a return loop so that it enters the transfer line as a jet or jets of liquid which agitate the liquid in the transfer line to a substantially uniform mixture, and removing a sample from the uniform mixture.

WO2013126732 discloses a system for measuring asphaltene content of crude oil, which includes a microfluidic chip, the microfluidic chip having a crude oil sample inlet port, a solvent port, a mixer and reactor section in fluid communication with the crude oil sample inlet port and the solvent port, and a filter in fluid communication with the mixer and reactor section, the filter having an inlet side and an outlet side, a waste port in fluid communication with the inlet side of the filter, and a product port in fluid communication with the outlet side of the filter.

SUMMARY

In the course of their developments, the Applicants have further developed their online crude oil monitoring technology in order to make it especially suitable to the new crude oils conveyed throughout the world, to their spectroscopy methodology, in particular to their near infra-red (NIR) spectroscopy methodology, and to the end-users who require regular and reliable online properties determinations for their crude oils.

Several technological challenges have been faced in the course of these developments amongst which can be cited: dealing with an increased proportion of heavy and/or unconventional crude oils and reducing the consumption of solvents throughout the process. The increased proportion of heavy and/or unconventional crude oils over the past years is inherent to the fact that less than thirty percent of the world oil reserves are recognised as conventional; there is thus more and more of heavy and/or unconventional crude oil which are conveyed in pipes throughout the world and which require online and reliable monitoring. Regarding the reduction in the amounts of solvents used in the course of the monitoring process, this objective is not only driven by environmental considerations but also because most of the crude oil pipes are monitored in remote locations where such solvent is either not available and/or not easy to supply. An additional challenge encountered during the developments was to maintain the (Near-Infrared) spectroscopic measurement material operational during long periods of time of operations without requiring intensive cleaning; indeed, the conventional methods proved that the said material become either irreversibly fouled or requiring regular burdensome cleaning due to the nature and characteristics of the crude oil.

In one first aspect, the present invention relates to a crude oil analytical and sampling device suitable for sampling safely and with accuracy crude oil from their conveying pipeline to the spectroscopy analysis device and comprising a fast loop system and a sample conditioning system cabinet which is connected to the spectroscopy analysis device characterised in that the fast loop comprises a filter (preferably a rotating filter) and a pump and the sample conditioning system cabinet comprises a grabber connected to the fast loop system, said grabber having a sampling volume Vgr comprised between 1 and 100 cubic centimeters (cm3), e.g. 1 and 10 cubic centimeters (cm3), a filter (preferably a large surface dual filter) and a double actuation syringe which has a sampling volume Vse comprised between 100 and 10 000 cubic centimeters (cm3) wherein a part or all of the sampling volume Vse is fed to the spectroscopy analysis device by the double actuation syringe and wherein the ratio between the syringe sampling volume (in cm3) Vse and the grabber volume (in cm3) Vgr is comprised between 50 and 500. Depending on the nature of crude oil product to analyze (e.g. density, viscosity, . . . ) and the specificity of the process to warrantee a determined analyzer answering time, the part or all of the sampling volume can be fed to the spectroscopy analysis device by the double actuation syringe continuously or not, preferably semi-continuously. According to a preferred embodiment of the present invention, one or more fractions of the Vse are fed to the spectroscopy analysis device by the double actuation syringe; the fractioning level could advantageously be modulated from 1 to 100. According to a preferred embodiment of the present invention, the number of fractions of crude oil product from the Vse fed to the spectroscopy analyzing device is comprised between 2 and 5, for example equals 3.

DETAILED DESCRIPTION

Figure 1:
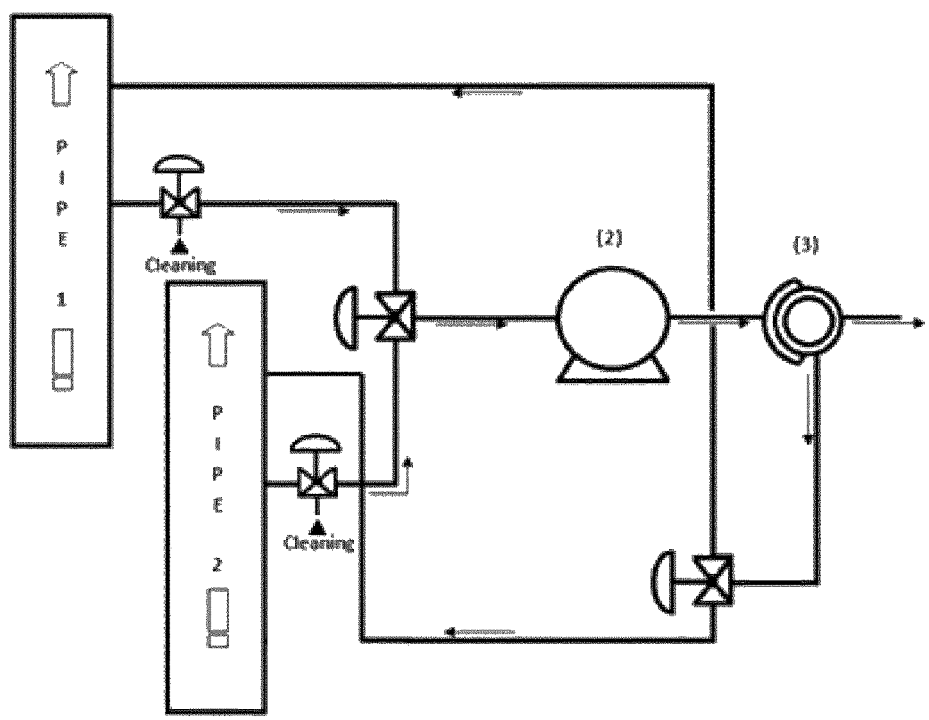
FIGS. 1, 2, 3 (3a, 3b, 3c), 4, 5 (5a, 5b, 5c, 5d, 5e) and 6 are illustrative embodiments of schemes according to the present invention.

FIG. 1 is an illustrative embodiment of two fast loops scheme configuration as detailed hereafter. In one optional embodiment, the crude oil analytical and sampling device according to the present invention comprises at least two fast loop systems which are connected to the same sample conditioning system cabinet, each fast loop system being connected to a different crude oil conveying pipeline and sharing the same filter (3) and pump (2). This embodiment is schematically represented in FIG. 1. Each fast loop shares the same filter (3) (preferably a rotating filter), the same pump (2) and an optional centrifugal separator. Each loop can analyze one or multiple products (called streams) flowing in one or multiple pipes. Each stream could be isolated from the other stream thanks to a selection valve that is preferably an automatic controlled pneumatic three ways valve. Each loop could be optionally connected to a piping system through the controlled pneumatic three ways valves for cleaning purposes.

In one alternative embodiment, the present invention relates to a method for crude oil sampling and analysis characterised by the use of a crude oil analytical and sampling device for sampling safely and with accuracy crude oil from their conveying pipeline to the spectroscopy analysis device and comprising a fast loop system and a sample conditioning system cabinet which is connected to the spectroscopy analysis device wherein the fast loop comprises a filter (preferably a rotating filter) and a pump and the sample conditioning system cabinet comprises a grabber connected to the fast loop system, said grabber having a sampling volume Vgr comprised between 1 and 100 cubic centimeters (cm3), e.g. 1 and 10 cubic centimeters (cm3), a filter (preferably a large surface dual filter) and a double actuation syringe which has a sampling volume Vse comprised between 100 and 10 000 cubic centimeters (cm3) wherein a part or all of the sampling volume Vse is fed to the spectroscopy analysis device by the double actuation syringe and wherein the ratio between the syringe sampling volume (in cm3) Vse and the grabber volume (in cm3) Vgr is comprised between 50 and 500.

In one additional alternative aspect, the present invention relates to a method for operating a spectroscopy analysis device during the analysis of crude oil, said spectroscopy analytical device (in particular its optical cell) using only mild cleaning treatments during operation wherein said spectroscopy analytical device is comprised in a crude oil analytical and sampling device for sampling safely and with accuracy crude oil from their conveying pipeline to the spectroscopy analysis device and comprising a fast loop system and a sample conditioning system cabinet which is connected to the spectroscopy analysis device wherein the fast loop comprises a filter (preferably a rotating filter) and a pump and the sample conditioning system cabinet comprises a grabber connected to the fast loop system, said grabber having a sampling volume Vgr comprised between 1 and 100 cubic centimeters (cm3), e.g. 1 and 10 cubic centimeters (cm3), a filter (preferably a large surface dual filter) and a double actuation syringe which has a sampling volume Vse comprised between 100 and 10 000 cubic centimeters (cm3) wherein a part or all of the sampling volume Vse is fed to the spectroscopy analysis device by the double actuation syringe and wherein the ratio between the syringe sampling volume (in cm3) Vse and the grabber volume (in cm3) Vgr is comprised between 50 and 500.

For the purpose of the present invention, "mild cleaning treatment" means the use on the active optical cell of the spectroscopic device, of one or more of the following treatments A to E:

A. Less than one (1) syringe volume (Vse) of flushing solvent for one (1) volume Vse of analyzed product, e.g. less than half of one (1) syringe volume (Vse) of flushing solvent for one (1) volume Vse of analyzed product. Said mild cleaning treatment A is preferably done at a time interval from 100 to even more than 240 minutes implying a daily flushing solvent consumption preferably inferior to 2*Vse, e.g. inferior to 1000 cubic centimeters (cm3) for an active optical cell of the spectroscopic device.

B. Less than twenty (20) cm3, e.g. less than ten (10) cm3 of flushing solvent for regular continuous cleaning that should preferably be used at a time interval from 60 to even more than 120 minutes implying a daily flushing solvent consumption preferably inferior to 1000 cm3 for an active optical cell of the spectroscopic device.

C. Less than thirty (30) cm3 of pure solvent for the spectroscopy device functioning validation that should preferably be used at a time interval from 240 to even more than 480 minutes, e.g. more than 12 hours or even more than 24 hours, implying a daily pure solvent consumption preferably inferior to 180 cm3 for an active optical cell of the spectroscopic device.

D. Less than 1 Sm3 instrument air preferably required for a blowing cleaning that should preferably be done at a time interval from 240 to even more than 480 minutes, e.g. more than 12 hours or even more than 24 hours, implying a daily air consumption preferably inferior to 6 Sm3 for an active optical cell of the spectroscopic device.

E. Less than 1 Sl nitrogen preferably required for a spectroscopic device validation that should preferably be done at a time interval from 240 to even more than 480 minutes implying a daily nitrogen consumption preferably inferior to 6 Sl for an active optical cell of the spectroscopic device.

For the purpose of the present invention, the flushing solvent is a general purpose aromatic or aliphatic product (e.g. at least 95% purity) preferably toluene.

For the purpose of the present invention, the pure solvent is a laboratory quality aromatic or aliphatic product (e.g. at least 99.5% purity) preferably pure toluene.

For the purpose of the present invention, the duration of the periods of operations without solvent cleaning (i.e. without any of treatment A, B and/or C) is at least 1 hour, preferably at least 90 minutes, at least 120 minutes, for example at least 150 minutes.

According to an embodiment of the present invention, the mild cleaning treatment includes at least two of the treatments A to E, for example at least three of said treatments. According to a preferred embodiment of the present invention, treatments A, C and E are performed; treatments B and/or D are optional. According to a preferred embodiment of the present invention, the mild cleaning treatment is advantageously characterised by a daily solvent (pure and flushing) consumption not exceeding 3000 cm3.

In another aspect, the present invention also provides a method of determining and/or predicting a value of a property of crude oil which comprises measuring the absorption of said oil at at least one wavelength in the region 600-2700 nm e. g. 600-2600 nm and converting that absorption (or derivative thereof) into a value of said property. The conversion may be direct, or indirect by statistical correlation or by non-correlation techniques. The application of near infra-red spectroscopy to the crude oil has been found to enable the data to be obtained on line or at line and very quickly, resulting in suitability for automated control techniques. In particular, the use of the near infra-red spectroscopy in combination with the claimed device and procedure allows the accurate and reliable measurement of an array of critical crude oil properties, e.g.: density, American Petroleum Institute gravity (API gravity), Total Acid Number (TAN), asphaltenes content, sulphur content and distillation curve—Simulated Distillation (Simdist) or True Boiling Points (TBP), the crude oil assays (for instance the yield of distillation cuts and residues both for atmospheric and vacuum distillation as well as other key properties of all distillation cuts and residues.

The crude oil is usually primarily aliphatic in nature, but may contain up to 50% by weight of liquid aromatic compounds. It is usually an oil field product from a well head, as whole well product i.e. the multiphase mixture from the well bore containing oil and water and/or gas which may be at 50-200 bar pressure, or preferably such product after at least partial removal of water and/or gas ready for sending away down a pipeline from the well head and may be at up to 50 bar e. g. 1-10 bar pressure. It may be on a production platform, or between platforms or from a production platform to a collection or storage facility, on or offshore, or vessel, or at such a collection or storage facility or downstream thereof e. g. in a pipeline downstream thereof e. g. at a further storage facility, such as in a gathering station or refinery or prior to a separation facility e. g. to separate gas and/or water and/or other components of the crude oil e. g. in a distillation to recover e. g. naphtha. The crude oil leaving the well head may contain dissolved gas (e. g. in amounts of up to 15% by weight gas e. g. 1-10% wt) and/or water or water droplets (e. g. 0.1-50% such as 0. 1-5% or 0.2-2%, or especially 1-40% such as 2-50% or 5-40% wt. water), while gas and/or water may be present as a physically separate phase especially when arriving at the well head; the Gas/Oil ratio (GOR) (expressed in StCu ft gas per barrel of oil) may be 1-10000 e. g. 2000-9000 (for oil arriving at a well head) and 1-1000 e. g. 50-500 or 1-50 e. g. 1-20 or 3-50 (especially for partly degassed oil leaving a well head). The crude oil may contain dissolved gaseous hydrocarbons e. g. methane, ethane, propane and butane (each in amounts of 0.1-5% e. g. 0.5-5% by weight or 0.1-10% e. g. 0.5-10% in the case of methane) and in total up to 15% especially to 10%. The oil may also be present with other gases e. g. inert gas such as nitrogen and carbon dioxide (each in amount of 0.1-5% such as 1-5 or 0.1-1%). In relation to the total weight of liquids in solution in the crude oil, the crude oil may contain 0-40% e. g. 10-30% gas condensates or light ends (which may be preferably in the amount relative to naphtha which was present in the well head crude oil, and so the analysed crude does not contain added condensates) 0-40% e. g. 20-40% by weight of naphtha, 5-30% e. g. 10-20% kerosene, 0-50% e. g. 5-40% or 20-30 gas oil, 0-40% e. g. 5-40% or 20-40% fuel oil (with residue). It may also contain (expressed on the same basis) 0-8% asphaltenes (e. g. 0.01-2%) 0-8% e. g. 1-7% or 0.05-2% sulphur and 0-10 e. g. 1-6 mg KOH/g as an expression of the acidity. The percentage composition of the total of dissolved gaseous hydrocarbons, gas condensates and light ends (expressed on the same basis) may be 5-50%, such as 10-40% especially 10-30% or 15-40%; such a combination may be that boiling at up to 130 C under atmospheric pressure. Its API gravity may be 10-60 e. g. 20-55 and its Pour Point −60 C to +60 C e. g. −20 C to +20 C. Its boiling range may be −30 C to 550 C and final boiling point up to 880 C. The oil may have been dewatered and/or desalted before analysis and in particular when analysed may be substantially free of any separate gas phase. It may be substantially free of dissolved gas when analysed, but preferably contains 0.1-15% dissolved gas. The oil being sampled may also contain up to 10% by weight suspended solids e. g. 1-5%.

The pipelines designed for conveying the crude oil have an inner diameter which is usually comprised between 2 inches and 52 inches pipeline. The present invention could be used for all types of crude oil pipelines, including the gathering lines which are very small pipelines usually from 2 to 8 inches in diameter and which can be used in the areas where crude oil is found deep within the earth (both onshore and offshore); however, the present invention is particularly suitable for the larger crude oil pipelines (also known as trunk lines), e.g. those measuring from 8 to 52 inches in diameter, preferably from 10 to 48 inches in diameter. In these conveying pipelines, the crude oil is usually kept in motion by pump stations along the pipeline, and usually flows at speed of about 1 to 6 meters per second.

With the increased proportion of heavy and/or unconventional crude oil conveyed through these pipelines all over the world the conventional crude oil property determination devices and techniques are facing critical fouling issues leading to both inaccuracies in the crude oil property determination and also in the use of huge amounts of solvents for cleaning the equipment.

Thus, in one first aspect, the present invention relates to a crude oil analytical and sampling device suitable for sampling safely and with accuracy crude oil from their conveying pipeline to the spectroscopy analysis device and comprising a fast loop system and a sample conditioning system cabinet which is connected to the spectroscopy analysis device characterised in that the fast loop comprises a filter (preferably a rotating filter) and a pump and the sample conditioning system cabinet comprises a grabber connected to the fast loop system, said grabber having a sampling volume Vgr comprised between 1 and 100 cubic centimeters (cm3), e.g. 1 and 10 cubic centimeters (cm3), a filter (preferably a large surface dual filter) and a double actuation syringe which has a sampling volume Vse comprised between 100 and 10 000 cubic centimeters (cm3) wherein a part or all of the sampling volume Vse is fed to the spectroscopy analysis device by the double actuation syringe and wherein the ratio between the syringe sampling volume (in cm3) Vse and the grabber volume (in cm3) Vgr is comprised between 50 and 500.

Thus, according to an embodiment of the present invention, one or more fractions of the sampling volume Vse are fed to the spectroscopy analysis device when required by the double actuation syringe. In an embodiment according to the present invention, at least two fractions, for example three fractions extracted from the sampling volume Vse of the double actuation syringe are fed to the spectroscopy analysis. These fractions are preferably of similar or preferably identical volumes; the total volume of these fractions represent preferably at least 50% of the sampling volume Vse of the double actuation syringe, for example at least 70%. The use of several fractions when required allows improving the accuracy and robustness of the spectroscopy measurement by either averaging the measurements performed on each fraction and/or by removing from the measurements the individual measurements which are too remote from the other measurements and thus indicative of errors. By increasing the number of fractions to ten fractions or even more, the Applicants believed that predictions accuracy should increase; therefore, the present invention could also be done in a continuous manner. In an embodiment according to the present invention, the Applicants have found that less than ten fractions allows to obtain the required accuracy in term of measurement and also to optimise the cleaning treatments and the operation lifetime of the spectroscopy device/optical cell.

According to an embodiment of the present invention, the grabber—which grabs the required volume of crude oil from the fast loop system and conveys it to the sample conditioning cabinet—has a sampling volume Vgr comprised between 1 and 100 cubic centimeters (cm3), e.g. between 1 and 10 cubic centimeters (cm3), preferably between 4 and 6 cm3, for example a Vg of 5 cm3.

According to an embodiment of the present invention, the double actuation syringe has a sampling volume comprised between 100 and 10 000 cubic centimeters (cm3), preferably between 100 and 1000 cm3, e.g. between 400 and 600 cm3. The double actuation syringes are preferably designed with specific materials (preferably Stainless Steel SS316L) that could have received beforehand specific physical or chemical treatments (like sulfur passivation treatment) to allow accepting all type of hydrocarbon products inside. As detailed in the figures, the double actuation syringe is a piston cylinder (preferably a floating type) having a sampling volume Vse with preferably a double hydraulic oil actuation pilot. For the purpose of the present invention, a double actuation syringe is a syringe wherein the fluid to be sampled (which is preferably pressurized) is first routed into the syringe which causes the piston to retract and is then routed (preferably in the opposite direction) outside the syringe towards the spectroscopy analysis device which causes the piston to extend. In a preferred embodiment, the syringe is equipped with a working fluid (for example compressed air and/or preferably incompressible oil) which acts alternately on both sides of the piston. The syringes are advantageously provided with an auto-cleaning of its cylinder wall which is operated by a scrapper on the double piston plate assembly.

In an embodiment according to the present invention, the ratio between each syringe sampling volume (in cm3) Vse and the grabber volume (in cm3) Vgr is comprised between 50 and 500, preferably between 75 and 150, for example 100.

The fast loop system according to the present invention, which can also be referred to as a fast loop sampler or bypass comprises at least one filter (preferably a rotating filter) and one pump. Said fast loop system is a pumped loop of diameter usually comprised between half inch and two inches which flows in parallel with the main crude oil pipeline. The loop size is usually selected as part of the design process to maximize sample accuracy, decrease analyser lag times and ensure sufficient velocity exists to maintain homogeneity of the fluids throughout the fast loop system. The fast loop system can be mounted into the crude oil pipeline through a seal housing allowing installation by hot tapping (i.e. by safely tying into a crude oil pipeline while it is on stream and usually under pressure) and removal under process conditions for pigging. An isolation valve is preferably installed directly downstream of the tapping fitting which connects to the crude oil pipeline. The crude oil flow can either be returned to the crude oil pipeline at the same point as extracted or at a suitable point up- or down-stream of the crude oil pipeline extraction point; when returned at another point up- or down-stream, an additional isolation valve is preferably installed directly upstream of the tapping fitting which connects to the crude oil pipeline.

Thus, the fast loop system according to the present invention comprises one or multiple filters and a pump. In a preferred configuration of the fast loop system according to the present invention, one or more optional filter(s) are added in the loop before the pump (upstream of the pump); said one or more optional filter(s) can be selected amongst well known pump protective filters—for example an Y-Strainer filter can advantageously be used. The pump is preferably located upstream the sampling system filter that could preferably be a rotative filter.

The pump used in the fast loop system according to the present invention can be selected by the man skilled in the art according to usual practice; said pump can e.g. be selected from centrifugal or volumetric pumps; example of a suitable volumetric pump is an API Reciprocating Displacement Pump delivering a controlled and accurate flow. API 674 & 675 pumps are preferably used; amongst the API 674 & 675 pumps, the Applicants have found that the metering pump with diaphragm pumphead is particularly suitable for their invention. Particularly preferred pumps are PTFE diaphragm with 1.4571 GR stainless steel suction and discharge valves. As disclosed here above, an Y-strainer filter could advantageously be used upstream the pump to protect it from the particles present in the crude oil.

Thus, the filters located in the fast loop system according to the present invention can be selected by the man skilled in the art according to usual practice; for the filter located downstream the pump, a rotating filter is particularly suitable for the crude oil, especially for the heavy and/or unconventional crude oils. Ideally, the rotating filter comprises a filter mesh of one hundred microns or less. The filtering media preferably consists of discs separated by spacers; the solid contaminants are stopped and removed during the rotation of the discs and fall down into the bottom of the housing where they are evacuated preferably through a drain to a recovery unit. The sequenced rotation is preferably performed by the mean of a pneumatic logic with actuator assembly consisting of rochet/actuator pulsed every time sequence, e.g. every 30 sec. The internal parts of the rotating filter are preferably made of stainless steel, more preferably selected from SAE grade 316 low carbon stainless steel family. The primary objective of the filter consists in removing from the crude oil all the particles exhibiting important dimensions, for example all the particles exhibiting a size superior or equal to 100 µm. An important part of the sediments present in the crude oil is removed during this step which contributes to the overall superior accuracy and repeatability of the continuous/semi-continuous online measurements performed according to the present invention.

Figure 2:
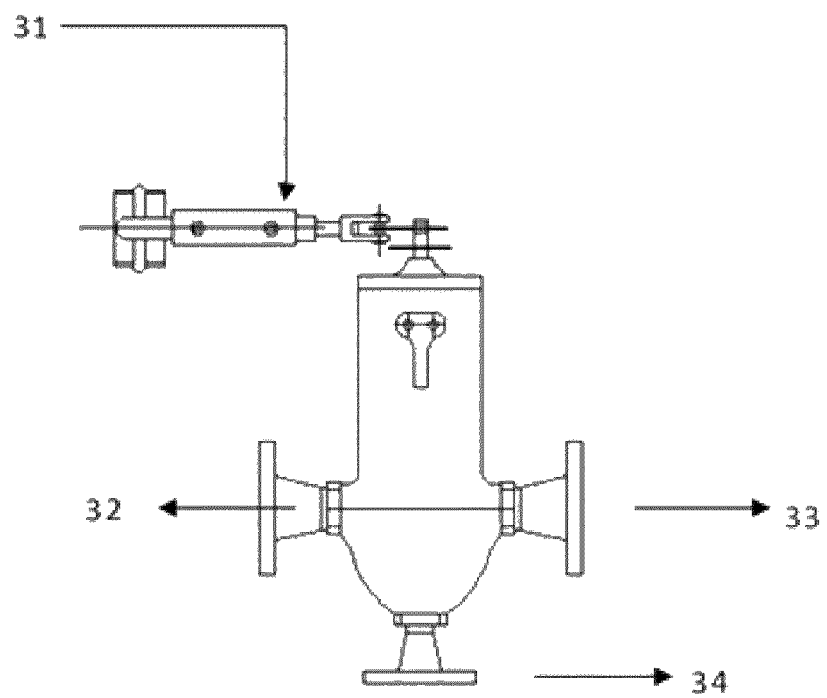

FIG. 2 is an illustrative embodiment of a rotative filter (3) as detailed hereafter. Thus, FIG. 2 illustrates an embodiment of the present invention which describes a rotative filter (3) where (31) is an actuator assembly consisting of rochet/actuator, (32) is the raw product (crude oil) inlet, (33) is the filtered product (crude oil) outlet and (34) is the drain. By using the said rotative filter, any kind of raw crude products could be processed in the present invention, even those crudes comprising important contaminants.

Figures 3A, 3B, 3C:
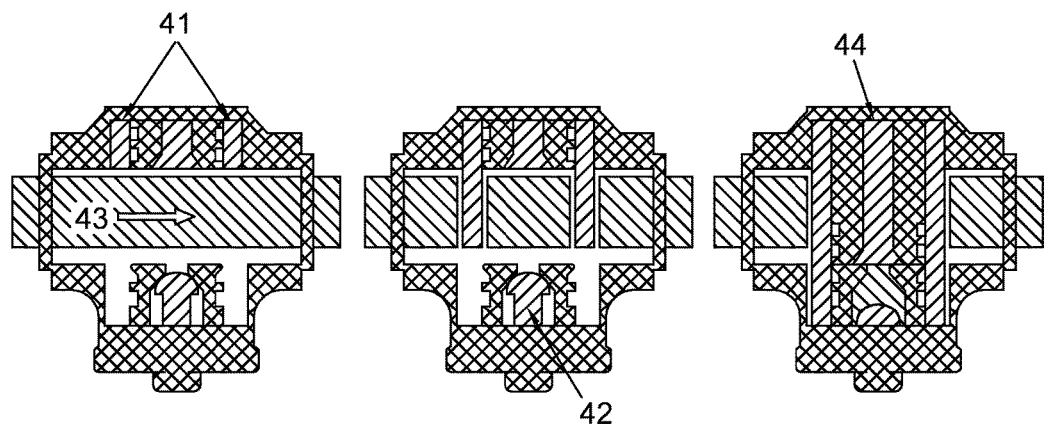

According to the present invention, a grabber is then used for extracting the crude oil sample from the fast loop. The said grabber has a sampling volume Vgr comprised between 1 and 100 cubic centimeters (cm3), e.g. between 1 and 10 cubic centimeters (cm3), for example 5 cm3+−1 cm3. Grabbers can be selected by the man skilled in the art according to usual practice; preferably, it incorporates features to minimize and simplify maintenance as well as providing integrity against leakages under all circumstances. FIG. 3 is an illustrative embodiment of a grabber (4) configuration as detailed hereafter. Thus, a preferred grabber (4) and the way it operates is schematically disclosed in FIG. 3. Said grabber comprises and acts like an air actuator piston. It comprises

(41) a capture tube, (42) a valve and (44) a piston. In this embodiment, the crude oil flows (43) from left to right. The air pressure on the piston moves the capture tube downwards for isolating and then expulsing a constant volume of sample through the valve towards the sample double actuation syringe. Conclusively, each stroke is introducing a calibrated sample volume into the sample double actuation syringe. FIGS. 3.a, 3.b and 3.c represent the said three consecutive sequences of the operating grabber. According to an embodiment of the present invention, the stroke frequency of the sampling grabber is function of the ratio ("R") between each syringe sampling volume Vse (in cm3) and the grabber sampling volume Vgr (in cm3); said stroke frequency is preferably comprised between R/20 per minute and R/5 per minute, preferably between R/12 per minute and R/8 per minute. For example, when R equals 100 (e.g. a syringe sampling volume Vse of 500 cm3 and a grabber sampling volume Vgr of 5 cm3), the frequency can advantageously be fixed at 10 strokes per minute (equivalent to R divided by 10); in said configuration it takes about 10 minutes for filling the syringe.

According to another embodiment of the present invention, the stroke frequency of the sampling grabber is constant and selected such that the duration of the filling of the syringe by the grabber is comprised between 5 and 20 minutes, for example between 8 and 12 minutes.

Thus, according to a preferred embodiment of the present invention the careful selection of the volume of grabber sampling, of the volume of the syringe and of the stroke frequency of the grabber allows to obtain improved accuracy and repeatability of the (semi-) continuous online measurements performed according to the present invention. An advantage of the said invention is that it does not require the use of complicated and heavy separation device like centrifugation separator. Indeed, rather than extracting crude oil contaminants like salt, waxy components and water, it has been noticed during successive laboratory experimentations, that sampling accurately into a syringe small aggregated volumes to be thereafter pulsed through the spectrometer optical cell (e.g. the optical cell disclosed in FR2915804A1) gave accurate and reliable results providing a precise control of volume size and number of cycles. This property is explained by the fact that the main problem occurring during analysis is the accumulation of contaminants on the optical cell elements and within small limits, the effects of these contaminants to the spectra resolution are negligible.

Whilst the present invention is applicable to any type of spectrometer, e.g. Raman, NMR, infrared, UV-visible, etc.; the Applicants have found that their claimed device and method are particularly useful for the near-infrared (NIR) spectroscopy.

Thus, in the one first aspect of the present invention, the crude oil sampling device suitable for sampling safely and with accuracy crude oil from their conveying pipeline to the spectroscopy analysis device comprises a sample conditioning system cabinet which is connected to the spectroscopy analysis device and which comprises a grabber, a filter (for example a large surface dual filter) and a double actuation syringe.

The filter in the sample conditioning system cabinet according to the present invention can be selected by the man skilled in the art according to usual practice; it is preferably selected amongst large surface dual filters. The said filter is preferably located directly after the outlet of grabber. The dual filter can advantageously be a small volume large surface element with automatic interchange. Differential pressure is monitored with alarm for the element to be replaced further to interchange. Maintenance periodicity is expected to exceed months thanks to surface element. The primary objective of the filter consists in removing from the crude oil the particles exhibiting a size superior or equal to 10 µm.

Figure 4:
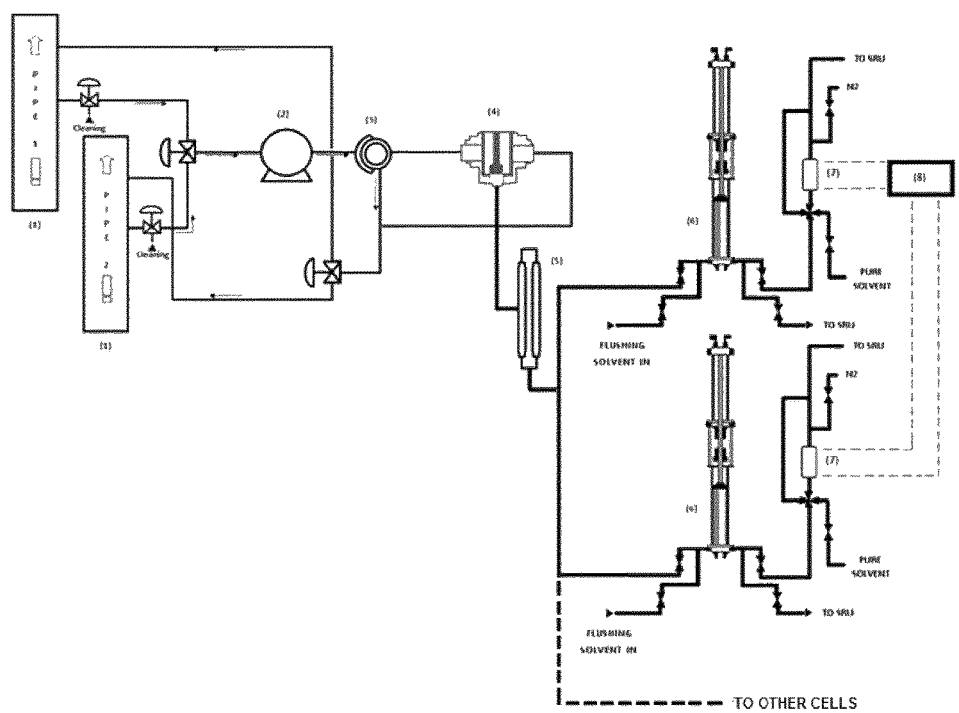

FIG. 4 is an illustrative embodiment of a crude oil sampling device and the way it operates. Thus, FIG. 4 illustrates an embodiment of the present invention which describes a crude oil sampling device which can advantageously be used in the present invention. Said crude oil sampling device comprises a fast loop system (which in FIG. 4 is represented as a two multi-stream fast loops scheme—which is a preferred embodiment according to the present invention) and a sample conditioning system cabinet. The crude oil which flows in the main pipelines (1) also flows continuously through the fast loop system. Said fast loop system comprises the pump (2) and the filter (3). Said sample conditioning system cabinet—which is connected to the spectroscopy analysis device (8) and an NIR cell (7)—comprises a grabber (4) having a sampling volume Vgr comprised between 1 and 100 cubic centimeters (cm3), e.g. between 1 and 10 cubic centimeters (cm3), a filter (5) (preferably a large surface dual filter) and double actuation syringes (6) which have each a sampling volume comprised between 100 and 10 000 cubic centimeters (cm3).

Figures 5, 5E:
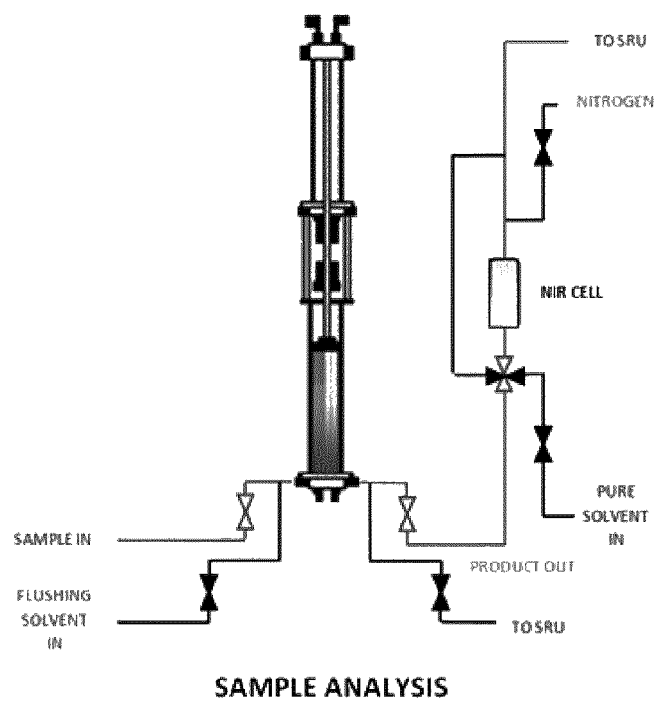

In order to illustrate the operations of the double actuation syringe according to the present invention, an example of one complete cycle of the said syringe operation is described hereafter in relation to FIG. 5 (FIGS. 5a, 5b, 5c, 5d, 5e): Originally the piston is in down position at the bottom plate with e.g. 2 barg pressure instrument air on the top of actuator.

1. Step 1 (not represented in the figures—corresponding illustrative embodiment is represented in FIG. 3): At start of the 10 minutes filling cycle, the grabber (Vgr of 5 cm3) pump introduces 5 cm3 per stroke into the syringe. Thus, a grab is operated every 7.5 sec. for 10 minutes cycle corresponding to 80 strokes equivalent to 400 cm3 of crude oil per 10 minutes of cycle.
2. Step 2 (FIG. 5e): At the end of the 400 cm3 filling in the syringe (Vse), 100 cm3 of the crude oil sample is pushed into the optical Cell circuit for a first flushing up to the 300 cm3 level: at this point the NIR first spectra is acquired.
3. Step 3: Two successive spectra are acquired as well at the 200 and 100 cm3 levels. In this example, from a 400 cm3 Vse, three fractions of 100 cm3 are analyzed.
4. Step 4: At the end analysis the remaining crude sampling volume of 100 cm3 in the Syringe is drained with piston pushed on bottom plate.

Further to this measuring cycle and each 10 cycles analysis (i.e. ten times three analyses which equal to 30 spectra), the Syringe (being in "stand-by" mode corresponding to FIG. 5a) and optical Cell circuit are cleaned and decontaminated with flushing fluid as explained hereafter; the optical Cell pure solvent like Toluene validation and Nitrogen zeroing are operated within the following steps:

5. Step 5: A 100 cm3 volume of flushing fluid is aspirated by the Syringe and re-injected into the Cell (FIG. 5b).
6. Step 6 (FIG. 5c): A 30 cm3 volume of pure solvent like Toluene is pushed in the Cell circuit by an additional separate piston cylinder (which is usually of a 100 L volume) described here under for cell validation (which can be done e.g. by toluene spectra comparison with corresponding toluene spectra which can be obtained from the literature, e.g. by superposition of said spectra).

7. Step 7: A volume of e.g. 1 Sm3 instrument air is drying the optical Cell circuit (not represented in the figures).
8. Step 8: A volume of e.g. 10 Sl Nitrogen is injected into the optical Cell circuit for zeroing (FIG. 5d).

During the period of the Syringe/Cell cleaning/decontamination according to one or more—preferably all of the above steps 5 to 8, another Syringe/Cell assembly is preferably operated.

According to an embodiment of the present invention, at least two double actuation syringes/cells assemblies are used.

In case of Syringe/Cell assembly non positive validation or zeroing a new complete cleaning cycle according to steps 5 to 8 cycle is preferably operated. Further to two unsuccessful cycles the assembly is declared "non valid for maintenance requirement".

Figure 6:
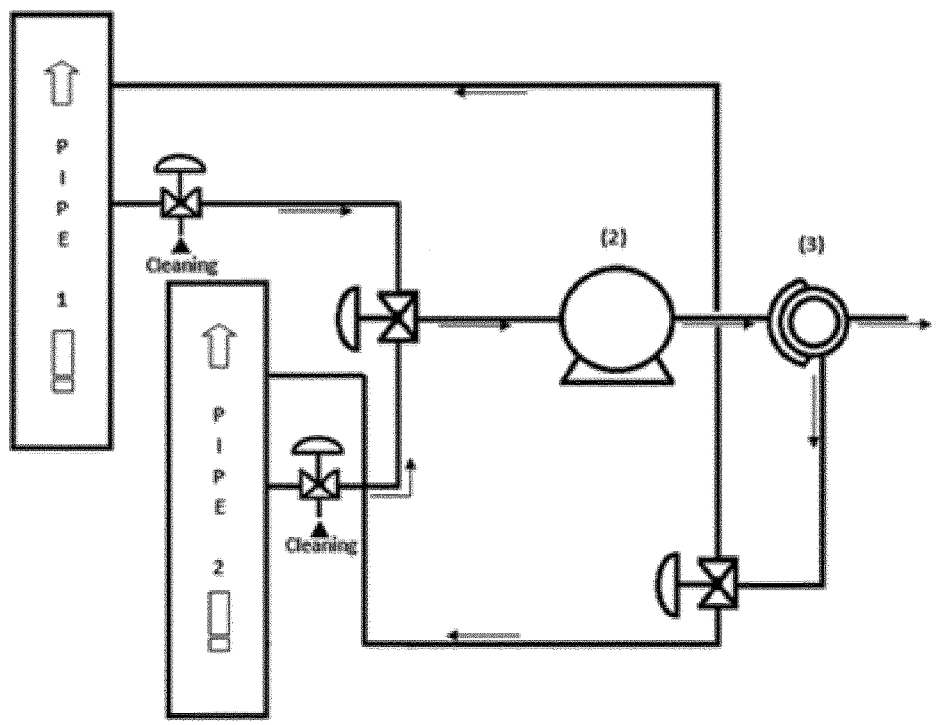

FIG. 6 illustrates an embodiment of the present invention which describes one Fast Loop that can analyze multiple crude oil streams: In the FIG. 6 scheme, samples from two different pipes are extracted. A pneumatic valve is used to allow the selection of the sample to analyze in the fast loop and that will flow through the pump (2) to go then to the filter (3) (preferably a rotative filter). The filtered product is orientated toward the analyzer sampling system and filter purge will go to a pneumatic selection valve that will send this return product either in pipe 1 or in pipe 2. The fast loop automation is entirely done by the analyzer multiplexer which makes this operation fully independent of human intervention.

In an embodiment according to the present invention, and as illustrated in FIG. 1, the present invention also relates to a single or multi-stream crude oil analytical and sampling device comprising one or more fast loop system(s) which are connected to a shared conditioning system cabinet, each fast loop of the analytical system being connected to one or more crude oil conveying pipeline(s), and sharing or not the same filter (3) and/or pump (2).

The present invention has been described in conjunction with specific embodiments thereof; the description cited above is intended to illustrate the present invention and not limit its scope. The figures are intended to give to the man skilled in the art a full disclosure and description of how to reproduce the invention, and are not intended to limit the scope of the present invention. Additional aspects, advantages and modifications will be apparent to the man skilled in the art.

What is claimed is:

1. Crude oil analytical and sampling device suitable for sampling crude oil from their conveying pipeline(s) (1) to a spectroscopy analysis device (8) and comprising a fast loop system connected to the crude oil conveying pipeline(s) and a sample conditioning system cabinet connected to the fast loop system and to the spectroscopy analysis device characterised in that the fast loop comprises a filter (3) and a pump (2) and the sample conditioning system cabinet comprises a grabber (4) connected to the fast loop system, said grabber having a sampling volume Vgr comprised between 1 and 100 cubic centimeters (cm3), a filter (5) and a double actuation syringe (6) which has a sampling volume Vse comprised between 100 and 10 000 cubic centimeters (cm3), said double actuation syringe being connected to the spectroscopy analysis device (8) for analysing a part or all of the sampling volume Vse wherein the ratio between the syringe sampling volume (in cm3) Vse and the grabber volume (in cm3) Vgr is comprised between 50 and 500.

2. A single or multi-stream crude oil analytical and sampling device according to claim 1 comprising one or more fast loop system(s) which are connected to a shared conditioning system cabinet, each fast loop of the analytical system being connected to one or more crude oil conveying pipeline(s), and sharing or not the same filter (3) and/or pump (2).

3. Crude oil analytical and sampling device according to claim 1 wherein the grabber sampling volume Vgr is comprised between 1 and 10 cubic centimeters (cm3), for example between 4 and 6 cubic centimeters (cm3).

4. Crude oil analytical and sampling device according to claim 1 wherein the double actuation syringe has a sampling volume Vse comprised between 100 and 1000 cubic centimeters (cm3).

5. Crude oil analytical and sampling device according to claim 1 wherein the ratio between each syringe sampling volume (in cm3) Vse and the grabber volume (in cm3) Vgr is comprised between 75 and 150.

6. Crude oil analytical and sampling device according to claim 1 wherein a stroke frequency of the sampling grabber is comprised between R/20 per minute and R/5 per minute, with "R" being defined as the ratio between each syringe sampling volume Vse (in cm3) and the grabber sampling volume Vgr (in cm3).

7. Crude oil analytical and sampling device according to claim 6 wherein the stroke frequency of the sampling grabber is between R/12 per minute and R/8 per minute.

8. Crude oil analytical and sampling device according to claim 1 wherein a fractioning level of the syringe sampling volume Vse is comprised between 1 to 100.

9. Crude oil analytical and sampling device according to claim 8, wherein the fractioning level of the syringe sampling volume Vse is lower than 10 fractions.

10. Crude oil analytical and sampling device according to claim 8, wherein the fractioning level of the syringe sampling volume Vse is between 2 and 5 fractions.

11. Crude oil analytical and sampling device according to claim 1 wherein the crude oil analytical and sampling device is configured to be used for crude oil sampling and analysis.

12. Crude oil analytical and sampling device according to claim 1 wherein a stroke frequency of the sampling grabber is constant and selected such that the duration of a filling of the syringe by the grabber is comprised between 5 and 20 minutes.

13. Crude oil analytical and sampling device according to claim 12, wherein the stroke frequency of the sampling grabber is selected such that the duration of the filling of the syringe by the grabber is between 8 and 12 minutes.

14. Crude oil analytical and sampling device according to claim 1 wherein the spectroscopy analysis device is a near-infrared (NIR) spectroscopy type.

15. Crude oil analytical and sampling device according to claim 1 further comprising:
   the spectroscopy analytical device including an optical cell; and
   a syringe configured to feed the spectroscopy analytical device;
   wherein the spectroscopy analytical device and the optical cell are subjected to one or more of the following cleaning treatments A to E:
   A feeding less than one (1) syringe volume (Vse) of flushing solvent for one (1) volume Vse of analyzed product to the spectroscopy analytical device using the syringe, said cleaning treatment A being done at a time interval from 100 to more than 240 minutes and implying a daily flushing solvent consumption inferior to 2*Vse for the optical cell of the spectroscopic device B feeding less than twenty (20) cm3 of flushing solvent for regular continuous cleaning to the spectroscopy analytical device using the syringe at a time interval from 60 to more than 120 minutes implying a daily flushing solvent consumption inferior to 1000 cm3 for the optical cell of the spectroscopic device C feeding less than thirty (30) cm3 of pure solvent for the spectroscopy device functioning validation to the spectroscopy analytical device at a time interval from 240 to more than 480 minutes, implying a daily pure solvent consumption inferior to 180 cm3 for the optical cell of the spectroscopic device D blowing cleaning using less than 1 Sm3 instrument air at a time interval from 240 to more than 480 minutes, implying a daily air consumption inferior to 6 Sm3 for the optical cell of the spectroscopic device E validating the spectroscopy analytical device using less than 1 Sl nitrogen at a time interval from 240 to more than 480 minutes implying a daily nitrogen consumption inferior to 6 Sl for the optical cell of the spectroscopic device.

16. Use of the device according to claim 15 wherein treatments A, C and E are performed.

17. Crude oil analytical and sampling device according to claim 16 wherein the duration of periods of operations in between any of treatment A, B and/or C is at least 1 hour.

18. Crude oil analytical and sampling device according to claim 17, wherein the duration of the periods of operations in between any of treatment A, B and/or C is at least 90 minutes.

19. Crude oil analytical and sampling device according to claim 17, wherein the duration of the periods of operations in between any of treatment A, B and/or C is at least 150 minutes.

20. Crude oil analytical and sampling device according to claim 15 wherein the daily solvent (pure and flushing) consumption is not exceeding 3000 cm3.

* * * * *